United States Patent [19]

Arndt et al.

[11] Patent Number: 4,983,415

[45] Date of Patent: Jan. 8, 1991

[54] METHOD OF MAKING PERMANENT IMAGES ON RECORDING SURFACE HAVING A THERMOSENSITIVE COLOR-DEVELOPING LAYER THEREON

[75] Inventors: Douglas C. Arndt, Thousand Oaks; Virgle L. Hedgcoth, Pomona, both of Calif.

[73] Assignee: Identicator Corporation, San Bruno, Calif.

[21] Appl. No.: 383,971

[22] Filed: Jul. 21, 1989

[51] Int. Cl.$^5$ ............................................. A61B 5/117
[52] U.S. Cl. ...................................................... 427/1
[58] Field of Search ................................... 427/1, 145

[56] References Cited

U.S. PATENT DOCUMENTS

| | | | |
|---|---|---|---|
| 4,029,012 | 6/1977 | Smith et al. | 118/31.5 |
| 4,232,083 | 11/1980 | Buerkley et al. | 427/1 |
| 4,705,299 | 11/1987 | Hedgcoth et al. | 427/1 |
| 4,879,134 | 11/1989 | Vassiliades | 427/1 |

FOREIGN PATENT DOCUMENTS

| | | | |
|---|---|---|---|
| 0053487 | 3/1983 | Japan | 427/1 |
| 2119314 | 11/1983 | United Kingdom | 427/1 |

*Primary Examiner*—Janyce Bell
*Attorney, Agent, or Firm*—Jackson & Jones

[57] ABSTRACT

An inkless method of recording an image of a desired object or symbol such as the print of a person's finger is described in which a recording surface is prepared by placing thereon a thermosensitive color-developing layer comprising a chromogenic dye such as a leuco dye, an organic acid developer, such as a phenolic compound, reactive with the dye to form a color and a thermosensitive barrier layer separating the dye and developer. A chemical reagent containing one or more metallic slats, such as ferric chloride, in the format of the desired object or symbol, is applied to the recording where the reagent reacts with the developer and/or dye in the thermosensitive color-developing layer to form a permanent two-dimensional image of the object or symbol such as the ridge pattern of the person's finger.

24 Claims, No Drawings

METHOD OF MAKING PERMANENT IMAGES ON RECORDING SURFACE HAVING A THERMOSENSITIVE COLOR-DEVELOPING LAYER THEREON

BACKGROUND OF THE INVENTION

1. Field of the Invention

The present invention relates to a method of recording an image of a desired object or symbol such as the print of a person's finger and, more particularly, to a method of providing a permanent print of such object or symbol on a recording surface containing a developing substance which reacts with an inkless reagent solution to form a colorant product representative of the object or symbol such as the ridge pattern of the person's finger.

2. Description of the Prior Art

Fingerprints have become a universal method of identifying individuals. Fingerprint identification is an exacting science since two impressions of even the same fingerprint can appear different due to variations in the amount of chemical, such as ink deposited onto the recording surface, chemical migration and changes in the finger itself. To determine an exact correspondence, a trained fingerprint technician or an automated machine reader compares the pattern of ridge endings and ridge bifurcations (minutiae) which are invariant with time on each person's fingerprint.

The prior art has recognized that any viable fingerprint identification system requires a clear distinct print pattern with a minimum of chemical migration between adjacent ridges. An additional requirement for any voluntary print identification system, such as to be utilized commercially with checks, credit verification and the like, is that it be inoffensive to the person whose fingerprint is being obtained. Ink fingerprinting systems are particularly offensive because the ink stains the finger and must be removed. Furthermore, ink systems tend to result in a smudging of the prints when the fingerprint cards, credit applications, checks, etc. are handled. Inkless fingerprinting systems have been developed to overcome the above disadvantages of ink systems.

See, for example, U.S. Pat. Nos. 4,182,261 and 4,262,623 assigned to the assignee of this application and the references cited therein. Inkless systems generally rely on a chemical reaction between an invisible reagent deposited onto a porous recording surface such as paper or a card in the form of a latent fingerprint image and a developer which is applied to the surface before or after the application of the reagent. The reagent and developer react chemically to form a colored pattern on the recording surface representative of the ridge pattern of a person's surface fingerprint. A large number of suitable reagent-developer pairs for this type of application are disclosed in U.S. Pat. Nos. 235,632, 4,029,012 and 4,182,261. It has also been suggested in U.S. Pat. No. 2,235,632 that the latent invisible fingerprint deposited from the person's finger on the recording surface maybe developed by a colorless powder, or volatile vapors comprising the developer or by the application of heat or intense light.

The application of a developer to the fingerprint paper or card just before or after the finger has deposited the reagent to provide the chemical reaction necessary to transform the invisible latent image into a visible one is time consuming and requires that an additional chemical be applied to the recording surface as compared with ink systems. The application of heat or intense light suffers from the obvious disadvantage that additional appendages to the fingerprinting apparatus, such as a heat or light source, may be required. Also, the operator of the fingerprinting apparatus cannot immediately judge whether or not the fingerprint taken is acceptable, since he or she has to wait until the print is developed by the application of the heat or light.

A need exists for an inkless fingerprint method which does not require the application of a second chemical (i.e., a developer) or heat or light to develop the latent invisible print. In a broader sense, a need exists for a method of permanently recording an image of an object or symbol on a thermosensitive recording paper or surface containing a thermosensitive color-developing layer thereon without the application of heat.

We have discovered that a substantially colorless solution containing a metallic salt when deposited in a pattern representative of an object to be reproduced, such as a fingerprint, onto a commercially available thermosensitive recording paper, as conventionally used in facsimile apparatus, will provide a permanent high contrast image of that object. We have further discovered that the application of heat is neither necessary nor desirable in such a method. Such thermosensitive recording paper includes a developer in the form of organic acid (e.g., one or more phenolic compounds) and a chromogenic substance (e.g., a colorless or pale dye such as a leuco or diazo dye). A heat sensitive barrier material generally in the form of a separation layer or protective covering encapsulating one of the reactants is normally included in such paper to prevent the chemicals from reacting absent the application of heat.

The metallic salt reacts with the organic acid (and also the dye in many cases) to provide the permanent image or print.

SUMMARY OF THE INVENTION

In accordance with the present invention, a thermosensitive recording surface is provided which contains a thermosensitive color-developing layer, the layer comprising a chromogenic dye and/or an organic acid developer reactive with the dye to develop a color. The layer also contains a thermosensitive barrier for preventing a reaction between the acid and dye. A solution of a chemical reagent containing one or more metallic salts is then formatted in a pattern to represent an object or symbol, such as a person's finger, the image of which is to be recorded. The solution in such pattern is then deposited onto the recording surface. The reagent reacts with the organic acid and/or dye in the thermosensitive color-developing layer to provide a two-dimensional permanent colorant product representative of the object or symbol. In terms of recording fingerprints, the solution is applied to the fingerprint area of at least one finger of a person to be fingerprinted. The solution of the chemical reagent on the ridges of the fingerprint pattern area is then deposited in a conventional manner on the recording surface. It should be noted that prints of a person's palms or feet may be made by the same method.

The features and steps of the present invention, which are believed to be novel, are set forth in the appended claims. This invention, as to its organization and advantages, may best be understood by reference to the following to be the following description.

BRIEF DESCRIPTION OF THE PREFERRED EMBODIMENT

The following description is provided to enable any person skilled in the art to make and use the invention and set forth the best mode contemplated by us of carrying out our invention.

In carrying out the invention with respect to recording fingerprints, a chemical reagent solution of one or more metallic salts is prepared and stored in a conventional dispensing pad which is nonreactive with the reagent. The pad should provide sufficient reagent to wet the ridge pattern of the person's finger without causing deleterious reagent migration between the ridges. Suitable materials for the pad include felt, porous plastics (i.e., polypropylene, polyethelene, etc.), rubber, animal hides and natural fibers (except those which contain starch). Porous ceramic or teflon may be used as the outer layer of the pad to control the flow rate of the reagent from the reservoir onto the person's finger, as is well known in the art. The reservoir for the reagent need not be in the form of a pad but also be in a sheet or other suitable form.

Preferably the metallic salt in the reagent is ferric chloride. However, salts of Titanium, Zirconium, Hafnium, Vanadium, Niobium, Tantalum, Chromium, Molybdenum, Tungsten, Manganese, Rhenium, Iron, Ruthenium, Cobalt, Rhodium, Iridium, Nickel, Palladium, Platinum, Copper, Silver, Gold, Zinc, Aluminum and Gallium may be used. The reagent also preferably contains a solvent for the metallic salt. Preferably the solvent is polyethylene glycol distributed under the trademark PEG200.

A preferred example of the reagent is:
1000 ml dipropylene glycol
300 g ferric chloride heyahydrate
10 ml Dowfax[1] 2A-1 surfactant

[1] Dowfax is a trademark of the Dow Chemical Company.

The recording surface may comprise a conventional thermosensitive recording paper as used in facsimile apparatus. Such paper, as discussed previously, includes a thermosensitive color-developing layer which comprises a chromogenic dye and an organic acid developer reactive with the dye to develop a color. A thermosensitive barrier for separating the acid from the dye may also be included.

One thermosensitive recording material suitable for use in this invention is described in U.S. Pat. No. 4,247,595 ("'595 patent"). As pointed out in the '595 patent, the chromogenic dye or substance may be selected from conventional colorless or pale-color leuco dyes such as "triphenylmethane, fluoran, phenothiazine, Auramine, spiropyran, etc. Examples of useful dyes include Crystal Violet lactone, Malachite Green lactone, 3,3-bis(p-dimethylphenyl)-6-aminophtalide, 3,3-bis(p-dimethylaminophenyl)-6-p-toluene sulfonamide, 3,3-bis(p-dimethylaminophenyl)-6-chlorophthalide, 3-dimethylamino-6-methoxyfluoran, 3-diethylamino-7-chlorofluoran etc.

While the above dyes are leuco dyes, it should be noted the diazo dyes may also be used.

The developer for reacting with the dye to develop the color may be a phenol compound such as "α-naphthol, β-naphthol, 4-t-octylphenol, 4-phenylphenol, 4-t-butylphenol, 4-hydroxyphenoxide, 4-hydroxyacetophenone, resorcine, hydroxynone, pyrogallol, phloroglucin, phloroglucin carboxylic acid, 4, 4'-sec-butylidenediphenol, 2,2-bis (p-hydroxyphenyl)propane, 2,2-bis(p-hydroxyphenyl)butane, 4,4'-cyclohexylidenediphenol, 2,2-bis(2,5-dibromo-4-hydroxyphenyl)propane, 4,4'-isopropylidene-bis(2-t-butylphenol), 2,2-methylene-bis(4-chlorophenol), 4-t-octylcatechol, 2,2'-dihydroxydiphenyl, 2,2'-methylene-bis(4-methyl-6-t-butylphenol), 2,2'-bis(4'-oxyphenyl)propane, 3,5-xylenol, etc.

The barrier material may be an inorganic filler such as calcium carbonate, titanium, oxide, clay, aluminum hydroxide, talc, silicin, magnesium carbonate, etc. A appropriate binder such as polyvinyl alcohol, gelatin, gum arabic, starch, etc., may also be used.

The '595 patent gives specific examples of the ingredients of thermosensitive color-developing liquids and the protocol for coating paper stock with the same to provide a recording surface suitable for use in our method. It should be noted that instead of placing a layer of thermosensitive color-developing layer on paper stock, such layer may be placed on any other suitable recording surface.

To record a finger, palm or footprint in accordance with my invention, a person's finger, palm or foot is coated with the solution of chemical reagent by pressing it against the reagent containing pad. The finger, palm or foot is then pressed or rolled onto the recording surface. The metallic salt reacts with the organic acid developer such as Bisphenol A to form a permanent perceivable colorant (generally black) precipitate within the thermosensitive layer representative of the ridge pattern of the person's finger, palm or footprint. The metallic salt is believed to combine with a hydroxyl group on the organic phenolic acid compound to develop the color. The metallic salt will also react with certain of the dyes incorporated in the thermosensitive color-developer layer to form a colorant precipitate. For example, we have determined that a solution ferric chloride will react with some leuco dyes (e.g., Copikem 4) to form a black colored precipitate and will not react with other dyes (e.g., Copikem 1 and leucomalachite green).

A permanent record of objects or symbols other than a person's finger may be made in accordance with the present invention by following the above method and simply by applying the chemical reagent in the desired format (e.g., representative of a symbol, etc., instead of a fingerprint pattern) to the recording surface containing the thermosensitive color-developing layer. For example, the chemical reagent in the desired format may be applied to the recording surface containing the thermosensitive color-developing layer by impact printing techniques, e.g. a brush, stamp, etc. or by non-impact printing techniques.

There has thus been described a simple and permanent inkless method for recording the image of a desired object onto a thermosensitive recording surface. With respect to fingerprints, the method is free (a) of any messiness and subsequent print smudging inherent in ink systems and (b) of the need for a second chemical or a source of heat or light to set the print as is required in the conventional inkless systems. The print is visible almost immediately so that the operator can judge whether or not the print is acceptable while the person being fingerprinted is still available for reprint.

As pointed out above, various modifications of the preferred embodiment may be made without departing from the spirit and scope of our invention.

What is claimed is:

1. A method of recording prints of a person's finger, palm or foot comprising:
   (a) providing a thermosensitive recording surface containing a thermosensitive color-developing layer, the layer comprising a chromogenic dye, an organic acid developer reactive with the dye to develop a color and a thermosensitive barrier for separating the acid and the dye;
   (b) applying a solution of a chemical reagent containing one or more metallic salts to the fingerprint, palm print or footprint area of a person whose finger, palms or foot is to printed;
   (c) depositing the solution of the chemical reagent from the ridges of the fingerprint, palm print or footprint pattern area to said recording surface whereby the chemical reagent reacts with the organic acid or dye or both to provide a permanent colorant product representative of the ridge pattern of the finger, palm or foot of said person.

2. The method of claim 1 wherein the developer includes one or more phenolic compounds.

3. The method of claim wherein the developer is comprised of bisphenol A.

4. The method of claim 1 wherein the metallic salts are selected from the group consisting of the salts of Titanium, Zirconium, Hafnium, Vanadium, Niobium, Tantalum, Chromium, Molybdenum, Tungsten, Manganese, Rhenium, Iron, Ruthenium, Cobalt, Rhodium, Iridium, Nickel, Palladium, Platinum, Copper, Silver, Gold, Zinc, Aluminum and Gallium.

5. The method of claim 4 wherein the metallic salt is ferric chloride.

6. The method of claim 1 wherein the chromogenic dye in the thermosensitive color-developing layer is reactive with the chemical reagent to form a permanent colorant product representative of the ridge pattern of the person's finger, palm or foot.

7. The method of claim 2 wherein the solution of chemical reagent comprises a mixture of ferric chloride, diethylene glycol, polyethylene glycol 200 and a surfactant.

8. A method of recording fingerprints comprising:
   (a) providing a thermosensitive recording surface containing a thermosensitive color-developing layer, the layer comprising a chromogenic dye, an organic acid developer reactive with the dye to develop a color and a thermosensitive barrier for separating the acid and dye;
   (b) applying a solution of a chemical reagent containing one or more metallic salts to the fingerprint area of at least one finger of a person to be fingerprinted;
   (c) depositing the solution of the chemical reagent from the ridges of the fingerprint pattern area to said recording surface whereby the chemical reagent reacts with the organic acid or dye or both to provide a permanent colorant product representative of the ridge pattern of the finger.

9. The method of claim 8 wherein the organic acid consists of a phenolic compound.

10. The method of claim 9 wherein the phenolic compound is bisphenol A.

11. The method of claim 9 wherein the metallic salts are selected from the group consisting of the salts of Titanium, Zirconium, Hafnium, Vanadium, Niobium, Tantalum, Chromium, Molybdenum, Tungsten, Manganese, Rhenium, Iron, Ruthenium, Cobalt, Rhodium, Iridium, Nickel, Palladium, Platinum, Copper, Silver, Gold, Zinc, Aluminum and Gallium.

12. The method of claim 11 wherein the metallic salt is ferric chloride.

13. The method of claim 12 wherein the solution of chemical reagent comprises a mixture of ferric chloride, diethylene glycol, polyethylene glycol 200 and a surfactant.

14. A method of making a permanent record of a desired object or symbol comprising:
   (a) providing a thermosensitive recording surface containing a thermosensitive color-developing layer, the layer comprising a chromogenic dye and an organic acid developer reactive with the dye to develop a color and a thermosensitive barrier for separating the acid and dye; and
   (b) applying a solution of a chemical reagent containing one or more metallic salts in the format of an image of the desired object or symbol to be recorded on the thermosensitive recording surface whereby the chemical reagent reacts with the organic acid to provide a permanent colorant product representative of the object or symbol.

15. The method of claim 14 wherein the developer includes one or more phenolic compounds.

16. The method of claim 15 wherein the developer is comprised of bisphenol A.

17. The method of claim 14 wherein the metallic salts are selected from the group consisting of the salts of Titanium, Zirconium, Hafnium, Vanadium, Niobium, Tantalum, Chromium, Molybdenum, Tungsten, Manganese, Rhenium, Iron, Ruthenium, Cobalt, Rhodium, Iridium, Nickel, Palladium, Platinum, Copper, Silver, Gold, Zinc, Aluminum and Gallium.

18. The method of claim 17 wherein the metallic salt is ferric chloride.

19. The method of claim 14 wherein the chromogenic dye in the thermosensitive color-developing layer is reactive with the chemical reagent to form a permanent colorant product representative of the object or symbol.

20. The method of claim 15 wherein the solution of chemical reagent comprises a mixture of ferric chloride, diethylene glycol, polyethylene glycol 200 and a surfactant.

21. A method of making a permanent two-dimensional record of a desired object or symbol comprising:
   (a) providing a paper containing a uniform layer of a chromogenic dye, an organic acid developer reactive with the dye to develop a color and a thermosensitive barrier separating the acid and dye; and
   (b) applying a solution of a metallic salt in the format of an image of the desired object or symbol on the paper whereby the metallic salt solution reacts with the organic acid or dye or both to provide a permanent colorant product representative of the object or symbol.

22. The method of claim 21 wherein the metallic salt is selected from the group consisting of the salts of Titanium, Zirconium, Hafnium, Vanadium, Niobium, Tantalum, Chromium, Molybdenum, Tungsten, Manganese, Rhenium, Iron, Ruthenium, Cobalt, Rhodium, Iridium, Nickel, Palladium, Platinum, Copper, Silver, Gold, Zinc, Aluminum and Galluim.

23. The method of claim 21 wherein the metallic salt is ferric chloride.

24. The method of claim 21 wherein the solution of metallic salt comprises a mixture of ferric chloride, diethylene glycol, polyethylene glycol 200 and a surfactant.

* * * * *

UNITED STATES PATENT AND TRADEMARK OFFICE
CERTIFICATE OF CORRECTION

PATENT NO. : 4,983,415

DATED : January 8, 1991

INVENTOR(S) : Arndt et al

It is certified that error appears in the above-identified patent and that said Letters Patent is hereby corrected as shown below:

Column 1, line 56, "235,632" should read --2,235,632--.

Signed and Sealed this

Seventh Day of July, 1992

Attest:

DOUGLAS B. COMER

*Attesting Officer*   *Acting Commissioner of Patents and Trademarks*